United States Patent
Choi et al.

(10) Patent No.: US 11,617,774 B2
(45) Date of Patent: Apr. 4, 2023

(54) COMPOSITION FOR PREVENTING OR TREATING STROKE OR DEGENERATIVE BRAIN DISEASE

(71) Applicant: UNIVERSITY-INDUSTRY COOPERATION GROUP OF KYUNG HEE UNIVERSITY, Gyeonggi-do (KR)

(72) Inventors: Jin Gyu Choi, Seoul (KR); Donghun Lee, Seoul (KR); Juyeon Park, Gyeonggi-do (KR); Jungbin Song, Seoul (KR); Hocheol Kim, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 0 days.

(21) Appl. No.: 15/917,209

(22) Filed: Mar. 9, 2018

(65) Prior Publication Data

US 2018/0256664 A1    Sep. 13, 2018

Related U.S. Application Data

(62) Division of application No. 14/785,312, filed as application No. PCT/KR2013/005301 on Jun. 17, 2013, now abandoned.

(30) Foreign Application Priority Data

Apr. 17, 2013    (KR) .................. 10-2013-0042048

(51) Int. Cl.
| | |
|---|---|
| A61K 36/63 | (2006.01) |
| A23L 33/115 | (2016.01) |
| A61K 35/60 | (2006.01) |
| A61K 31/201 | (2006.01) |
| A61K 31/23 | (2006.01) |
| A61K 31/685 | (2006.01) |
| A23G 1/42 | (2006.01) |
| A23G 4/12 | (2006.01) |
| A61K 31/047 | (2006.01) |
| A61K 9/00 | (2006.01) |
| A61K 36/48 | (2006.01) |

(52) U.S. Cl.
CPC .............. *A61K 36/63* (2013.01); *A23G 1/42* (2013.01); *A23G 4/12* (2013.01); *A23L 33/115* (2016.08); *A61K 9/0019* (2013.01); *A61K 31/047* (2013.01); *A61K 31/201* (2013.01); *A61K 31/23* (2013.01); *A61K 31/685* (2013.01); *A61K 35/60* (2013.01); *A61K 36/48* (2013.01); *A23V 2002/00* (2013.01)

(58) Field of Classification Search
CPC ........ A23L 33/115; A61K 36/63; A61K 36/48
See application file for complete search history.

(56) References Cited

U.S. PATENT DOCUMENTS

| | | | | |
|---|---|---|---|---|
| 5,994,322 | A * | 11/1999 | Masuda | A61K 31/688 514/52 |
| 8,193,245 | B2 | 6/2012 | Kim et al. | 514/17.7 |
| 2008/0227860 | A1 | 9/2008 | Kim et al. | 514/560 |
| 2010/0226932 | A1 | 9/2010 | Smith et al. | |
| 2011/0044944 | A1 | 2/2011 | Theoharides | 424/85.4 |
| 2011/0200644 | A1* | 8/2011 | Lee | A61K 9/0019 424/400 |
| 2013/0137770 | A1 | 5/2013 | Lewis | 514/560 |
| 2016/0008414 | A1 | 1/2016 | Kim et al. | 424/725 |

FOREIGN PATENT DOCUMENTS

| | | | | |
|---|---|---|---|---|
| CN | 1839819 | A * | 10/2006 | |
| CN | 101199478 | A * | 6/2008 | |
| CN | 101953856 | | 1/2011 | |
| CN | 101953856 | A | 1/2011 | |
| CN | 102106819 | | 6/2011 | |
| CN | 102232429 | A * | 11/2011 | |
| CN | 102526065 | A * | 7/2012 | |
| JP | 07025760 | | 1/1995 | |
| KR | 10-0756890 | | 9/2007 | |
| WO | WO 2007/021061 | | 2/2007 | |
| WO | WO 2007/021061 | A1 | 2/2007 | |
| WO | WO-2009045481 | A1 * | 4/2009 | ........... A61K 31/198 |

(Continued)

OTHER PUBLICATIONS

Medline Plus. "Degenerative Nerve Diseases". Page last updated on Jun. 8, 2021. Topic last reviewed: Apr. 29, 2014. Retrieved from the Internet on: Jul. 2, 2021. Retrieved from: <URL: https://medlineplus.gov/degenerativenervediseases.html#>. (Year: 2021).*

MayoClinic Amyotrophic lateral sclerosis (ALS). Retrieved from the Internet on: Jul. 2, 20201. Retrieved from: URL: <https://www.mayoclinic.org/diseases-conditions/amyotrophic-lateral-sclerosis/diagnosis-treatment/drc-20354027?p=1>. (Year: 2021).*

UCSFHealth. Creutzfeldt-Jakob disease treatments. Retrieved from the Internet on: Jul. 2, 20201. Retrieved from: URL: <https://www.ucsfhealth.org/conditions/creutzfeldt-jakob-disease/treatment>. (Year: 2021).*

(Continued)

*Primary Examiner* — Amy L Clark
(74) *Attorney, Agent, or Firm* — Potomac Law Group, PLLC

(57) ABSTRACT

The present invention relates to a composition for preventing and/or treating a stroke or a degenerative brain disease comprising: at least two substances selected from the group consisting of egg yolk lecithin, glycerol, sodium oleate, medium chain triglyceride and refined fish oil; olive oil; and soybean oil. The composition of the present invention has an excellent neuroprotective effect but no toxicity or side effects, and thus can be effectively and safely used for preventing, treating or ameliorating a stroke or a degenerative brain disease.

3 Claims, 1 Drawing Sheet

(56) References Cited

FOREIGN PATENT DOCUMENTS

| | | |
|---|---|---|
| WO | WO 2011/133841 | 10/2011 |
| WO | WO 2011/133841 A2 | 10/2011 |
| WO | WO 2013/127727 | 9/2013 |
| WO | WO 2013/127727 A1 | 9/2013 |

OTHER PUBLICATIONS

MayoClinic: Parkinson's Disease. Retrieved from the Internet on: Jul. 2, 20201. Retrieved from: URL: <https://www.mayoclinic.org/diseases-conditions/parkinsons-disease/diagnosis-treatment/drc-20376062?p=1 >. (Year: 2021).*

Database WPI Week201133, Thomson Scientific, London, GB AN 2011-D17677 XP002763471, Jan. 26, 2011.

"Food" definition. Retrieved from the internet, https://www.google.com/?gws_rd=ssl#q=food+definition &spf=1496528443105, Jun. 3, 2017.

Letter/Written Disclosure of the Supplemental Information Disclosure Statement filed on Mar. 14, 2017 for U.S. Appl. No. 14/785,312, 2 pages.

Letter/Written Disclosure of the Information Disclosure Statement for the above-referenced application, dated Jan. 28, 2016, 2 pages.

De La Cruz et al., "Effect of virgin olive oil plus acetylsalicylic acid on brain slices damage after hypoxia-reoxygenation in rats with type 1-like diabetes mellitus." Neurosci Lett. 471(2):89-93 (2010).

Drug Info Database, Medical Supplies Search, Clinoleic 20% Injection 1000 ml; available at http://www.druginfo.co.kr/cp/msd/detail/product_cp.aspx?cppid=47669 [published Mar. 2, 2012] Bit Computer Co. Ltd, [retrieved Mar. 26, 2015] [partial English translation], 1 page.

Flowers F & Zimmerman, J.J., "Reactive oxygen species in the cellular pathophysiology of shock." New Horiz. 6:169-180 (1998) [abstract only; available at http://www.ncbi.nlm.nih.gov/pubmed/?term=Flowers+F%2C+Zimmerman+JJ.+New+Horiz.+6%3A169-180%2C+1998].

Gonçalves-de-Albuquerque et al., "Oleic acid induces lung injury in mice through activation of the ERK pathway." Mediators Inflamm. 2012:956509 (2012).

Kalin, M.F. & Zumoff, B., "Sex hormones and coronary disease: a review of the clinical studies." Steroids. 55:330-352 (1990).

Kang et al., "Chronological changes of N-methyl-D-aspartate receptors and excitatory amino acid carrier 1 immunoreactivities in CA1 area and subiculum after transient forebrain ischemia." J. Neurocytol. 30:945-955 (2001).

Kirino T. & Sano K.,"Selective vulnerability in the gerbil hippocampus following transient ischemia." Acta Neuropathol. 62(3): 201-208 (1984).

Kirino T., "Delayed neuronal death in the gerbil hippocampus following ischemia." Brain Res. 239:57-69 (1982).

Lee et al., "Oleic Acid Decreased Brain Infarct Volume in Middle Cerebral Artery Occlusion Rats by Peroxisome Proliferator-Activated Receptor γ Activation." International Stroke Conference 2013 Presentation Abstract P30, Feb. 5-8, 2013; Oasis [retrieved Apr. 16, 2013], 2 pages.

Longa et al., "Reversible middle cerebral artery occlusion without craniectomy in rats." Stroke. 20(1):84-91 (1989).

Mohagheghi et al., "Dietary virgin olive oil reduces blood brain barrier permeability, brain edema, and brain injury in rats subjected to ischemia-reperfusion." ScientificWorldJournal. 10:1180-1191 (2010).

Oh et al., "Oleic acid reduces lipopolysaccharide-induced expression of iNOS and COX-2 in BV2 murine microglial cells: possible involvement of reactive oxygen species, p38 MAPK, and IKK/NF-kappaB signaling pathways." Neurosci Lett. 464(2):93-97 (2009).

Samieri et al., "Olive oil consumption, plasma oleic acid, and stroke incidence." Neurology. 77(5):418-425 (2011).

Sun A.Y. & Chen, Y.M., "Oxidative stress and neurodegenerative disorders." J. Biomed. Sci. 5:401-414 (1998).

Tang et al., "Susceptibility to fatty acid-induced β-cell dysfunction is enhanced in prediabetic diabetes-prone biobreeding rats: a potential link between β-cell lipotoxicity and islet inflammation." Endocrinology. 154:89-101 (2013).

Tomsits et al. "Safety and efficacy of a lipid emulsion containing a mixture of soybean oil, medium-chain triglycerides, olive oil, and fish oil: A randomised, double-blind clinical trial in premature infants requiring parenteral nutrition." Journal of Pediatric Gastroenterology & Nutrition. 51(4):514-521 (2010).

Wang et al., "Alveolar permeability enhancement by oleic acid and related fatty acids: evidence for a calcium-dependent mechanism." Pharm. Res. 11:513-517 (1994).

Wang et al., "Effect of endogenous hydrogen sulfide on oxidative stress in oleic acid-induced acute lung injury in rats." Chin. Med. J. 124(21):3476-3480 (2011).

Won et al., "Immunohistochemical detection of oxidative DNA damage induced by ischemia-reperfusion insults in gerbil hippocampus in vivo." Brain Res. 836:70-78 (1999).

International Search Report and Written Opinion, dated Dec. 30, 2013, in connection with International Patent Application No. PCT/KR2013/005301, 12 pages [English translation].

Official Action, dated Apr. 1, 2015, in connection with Korean Patent Application No. 10-2013-0042048, 9 pages [Original document in Korean with English translation].

International Preliminary Report on Patentability, dated Oct. 20, 2015, in connection with International Patent Application No. PCT/KR2013/005301, 9 pages [English translation].

Letter/Written Disclosure of the Supplemental Information Disclosure Statement for the above-referenced application, filed herewith on Sep. 7, 2017, 2 pages.

ClinOleic 20% Emulsion for Infusion Package Leaflet: Information for User, last revised Sep. 2014, Baxter, 2 pages.

ClinOleic Product Information, last revised Sep. 2014, Baxter Healthcare, 13 pages.

"Highlights of Prescribing Information: SMOFLIPID (Lipid Injectable Emulsion), for Intravenous Use." revised May 2016, Fresenius Kabi, 19 pages.

Response, filed Jun. 12, 2017, to Extended European Search Report, dated Nov. 22, 2016, in connection with corresponding European Patent Application No. 13882359.6, 9 pages.

Letter/Written Disclosure of the Supplemental Information Disclosure Statement for the above-referenced application, filed herewith on Dec. 21, 2016, 2 pages.

Database WPI Week 201133 [published on Jan. 26, 2011], Thomson Scientific, London, GB; AN 2011-D17677, XP002763471, & CN 101 953 856 A, 2 pages.

Extended European Search Report, dated Nov. 22, 2016, in connection with corresponding European Patent Application No. 13882359.6, 9 pages.

* cited by examiner

[FIG.1]
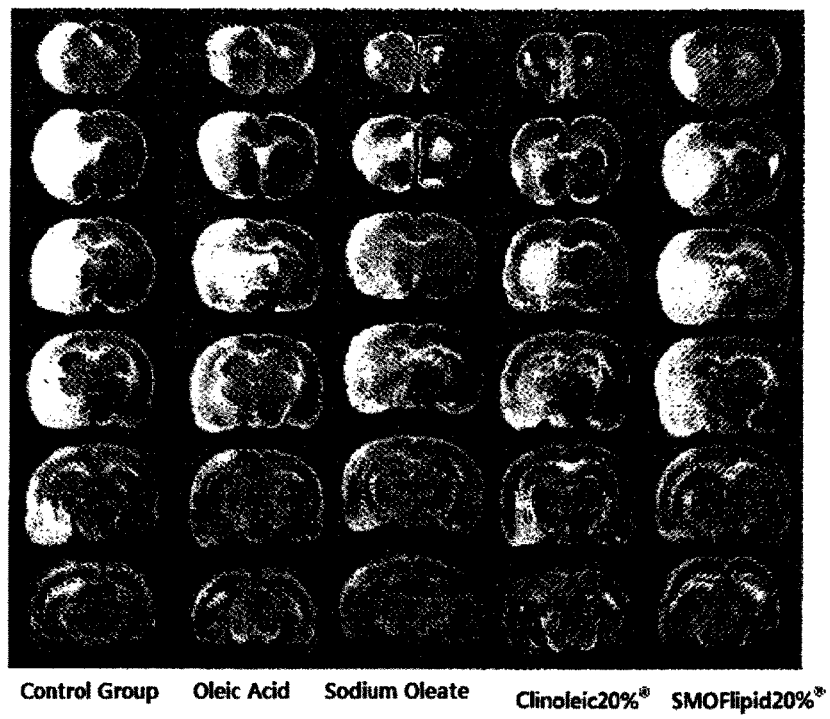
[FIG. 2]
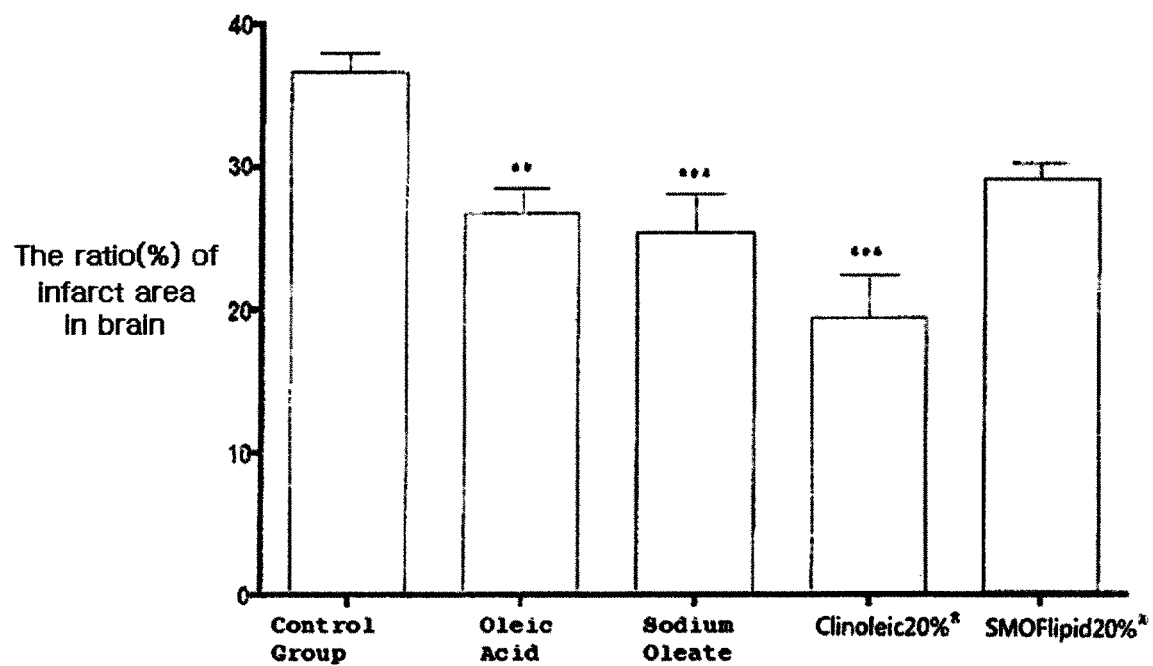

COMPOSITION FOR PREVENTING OR TREATING STROKE OR DEGENERATIVE BRAIN DISEASE

BACKGROUND OF THE INVENTION

1. Field of the Invention

The present invention relates to a composition for preventing or treating stroke or degenerative brain disease.

2. Description of the Related Art

According to the report released by the Statistics Korea (2010), population ratio of aged people over 65 in 2011 in Korea takes 11.4% and it is expected to become a super-aged society with 37.4% of population ratio in 2050. This aging problem is being treated as a social issue recently and accordingly, public interest on welfare for seniors such as characteristics of aged population, housing, welfare, culture and leisure among others are increasing as well as increasing needs for related statistics. The essence of this change is that chronic degenerative diseases are being a bigger problem than acute infectious diseases which have been a major cause of death for past 50 years due to increasing population of aged people. Especially, death from cerebrovascular disease among chronic degenerative diseases is a significant disease which is the second biggest cause of death resulted from single disease.

These cerebrovascular diseases can be categorized into 2 types. One is hemorrhagic brain disease such as cerebral hemorrhage, and the other is ischemic brain disease caused by cerebrovascular occlusion, etc. Major cause of hemorrhagic brain disease is car accidents and ischemic brain diseases are mainly observed among the elders.

When transient cerebral ischemia is induced in cerebrum, ATP reduction and edema in nerve cell incur due to oxygen and glucose supply cut-off, and accordingly leads to massive damage in brain. Neuronal cell death comes long time after occurrence of cerebral ischemia, and this phenomenon is called a delayed neuronal death. According to an experiment on delayed neuronal death through transient forebrain ischemic model wherein a Mongolian gerbil is used, it is reported that neuronal cell death is observed in CA1 region of hippocampus 4 days after 5 minutes of cerebral, ischemia induction (Kirino T, Sano K. Acta Neuropathol., 62:201-208, 1984; Kirino T. Brain Res., 239:57-69, 1982).

So far, there are two widely known mechanisms for neuronal cell death caused by cerebral ischemia. One is an excitatory neuronal cell death mechanism (Kang T C, et al., J. Neurocytol., 30:945-955, 2001) in which neuronal cell death is induced by an excessive accumulation of calcium in cells due to influx of excessively accumulated glutamate at outside of caused by cerebral ischemia, and the other is oxidative neuronal cell death in which neuronal cell death is induced by damages to DNA and cytoplasm due to increment of in vivo radicals caused by sudden oxygen supply at the time of ischemia-reperfusion (Won M H, et al., Brain Res., 836:70-78, 1999; Sun A Y., Chen Y M., J. Biomed. Sci., 5:401-414, 1998; Flowers F, Zimmerman J J. New Horiz. 6:169-180, 1998).

Based on the study of mechanism, researches to search for substances which effectively inhibit neuronal cell death caused by cerebral ischemia and unravel the mechanism of such substances are being conducted. However, barely no substances that inhibit neuronal cell death caused by cerebral ischemia exist up to the present.

Tissue plasminogen activator, currently on sale under FDA approval, is the only therapeutic agent for cerebral ischemia which is a thrombolytic agent that induces fast supply of oxygen and glucose by dissolving thrombus that induces cerebral ischemia. Thus, quick use is required because it does not protect neuronal cell cells directly; moreover, because of its characteristic of thrombolytic agent, it eventually induces hemorrhagic brain diseases due to thinned blood vessel wall when using it excessively or frequently. Additionally, clinical test on MK-801 (i.e. calcium channel blocker) was conducted to effectively inhibit initial calcium influx but drugs were discarded because of its side effects. Edaravone (i.e. synthetic antioxidant, Mitsubishi, Japan) was the only medicine for ischemic stroke which passed clinical test with successful result and prescribed only in Japan, but even with its possible side effects, it has a yearly turnover of 300 billion Korean Won because there are no alternative for the drug.

Over analyses on possible causes of development failure, it is most persuasive that the substances are synthetic which are not originated from natural resources. Therefore, it is important to develop with candidate substances existing in natural products. The present inventors confirmed significant protective efficacy of HP074 85% alcohol extract and its hexane fraction in a transient local cerebral ischemia rat model and a transient forebrain ischemia rat model (KR Patent Registration No. 10-2005-0076324). They also confirmed that oleic acid, a component of hexane fraction, has superior neuroprotective efficacy in local cerebral ischemia model, and confirmed the mechanism further through both in vivo and in vitro.

The present inventors confirmed that oleic acid increases death rate with its toxicity and its cause can be assumed by various documents teaching that pulmonary edema is caused in various animal models (Mediators Infalamm. 2012; 2012: 956509. Doi:10.1155/2012/956509.Epub 2012 Nov. 13) (Chin Med J 2011; 124(21):3476-3480). Document related to pulmonary edema induction model by using oleic acid is also reported. Oleic acid incurs erythroclasis (hemolysis) in an in vitro test, and thus excessive ingestion or intravenous injection of oleic acid can be harmful (Pharm Res 1994; 11:513 517). Furthermore, LD50 value of oleic acid is known to be relatively low as intravenous 2.4 mg/kg in rat. Oleic acid is in form of free fatty acid, and oleic acid included in olive oil exists as triglycerides, and the increase of free fatty acid promotes gluconeogenesis, induces insulin resistance in liver and muscle, and results in insulin secretion disorders. Said impairments caused by free fatty acid are called lipotoxicity (Endocrinology 2013 154:89-101). In addition, lots of problems still lie in utilization regarding cost and safety.

Olive oil as a natural product has oleic acid as a main ingredient and it is generally understood as a non-irritating and nontoxic substance. LD50 value of olive oil is intravenous 1320 mg/kg in mouse that is much higher than that of oleic acid and accordingly, it can be evaluated as safe. Additionally, oleic acid, which is a main ingredient of olive oil, is in form of triglycerides and it is known to be safer than form of free fatty acid. A thesis of epidemiologic survey wherein risk of stroke decreases as oleic acid concentration in blood plasma increased by ingesting olive acid has been published (Neurology. 2011 Aug. 2; 77 (5):418-25). Also, a document wherein antioxidant and anti-inflammatory effects and platelet aggregation are increased after ingestion of olive oil has been reported (The Scientific World JOURNAL (2010) 10, 1180-1191), (Neuroscience Letters 471 (2010) 89-93). Therefore, it could be understood that protective effect of neuronal cells is caused by activation of oleic acid, and pharmacological mechanism of oleic acid is reported in a paper (Neuroscience Letters 464 (2009) 93-97).

Succeedingly, the present inventors invented the present invention as a result of research to develop a composition comprising olive oil as a safe and effective therapeutic agent.

SUMMARY OF THE INVENTION

It is a purpose of the present invention to provide a composition for preventing or treating stroke or degenerative brain disease having no toxicity and side effects.

The present invention provides a pharmaceutical composition for preventing or treating stroke or degenerative brain disease comprising at least two substances selected from a group consisting of egg yolk lecithin, glycerol, sodium oleate, medium chain triglyceride and refined fish oil; olive oil; and soybean oil.

The egg yolk lecithin is a lecithin having phospholipid components obtained from egg yolk.

The glycerol is a substance having the rational formula $CH_2OHCH(OH) CH_2OH$, 92.09382 g/mol of molecular weight, 1.2644 g/cm$^3$ (15° C.) of specific gravity, 17.8° C. of melting point and 290° C. of boiling point. It is colorless, transparent and sticky liquid with sweet taste, and has high hygroscopicity.

The sodium oleate is sodium salt of oleic acid.

The medium chain triglyceride whose fatty acids have an aliphatic tail of 8-12 carbon atoms, and it is an ester derived from glycerol, and three fatty acids.

The refined fish oil is a refined oil of marine animals.

The olive oil is a vegetable oil contained in fruits of an olive tree (*canarium album*) that is obtained by squeezing or extracting its pulp directly. Fatty acid of the olive oil is composed of 76% of oleic acid (i.e. unsaturated fatty acid), 8% of linoleic acid, 12% of palmitic acid (i.e. saturated fatty acid) and 2% of stearic acid.

The soybean oil (18-20% content) is semidrying oil derived from soybean. Fatty acid of the soybean oil is composed of 55% of linoleic acid (i.e. unsaturated fatty acid).

As a preferred embodiment of the present invention, the composition includes 0.1-20.0 wt % of the olive oil, 0.1-20.0 wt % of the soybean oil, 0.1-20.0 wt % of the medium chain triglyceride and 0.1-10 wt % of the refined fish oil. As a more preferred embodiment of the present invention, the composition includes 6 wt % of the olive oil, 6 wt % of the soybean oil, 6 wt % of the medium chain triglyceride and 3 wt % of the refined fish oil. The composition ratio was a result of the inventors' research on a composition which would exhibit low toxicity and side effects while having superior neuroprotective effect. SMOFlipid 20% Injection that is prepared and sold by the Fresenius-Kabi Korea; can be used as a most preferred composition of the present invention.

As a preferred embodiment of the present invention, the composition includes 1.0-50 wt % of olive oil, 0.1-20 wt % of soybean oil, 0.01-5 wt % of egg yolk lecithin, 2.25 wt % of glycerol and 0.01-1.0 wt % of sodium oleate. As a more preferred embodiment of the present invention, the composition includes 16 wt % of olive oil, 4 wt % of soybean oil, 1.2 wt % of egg yolk lecithin, 2.25 wt % of glycerol and 0.03 wt % of sodium oleate. The composition ratio was a result of the inventors' research on a composition which would exhibit low toxicity and side effects while having superior neuroprotective effect. Clinoleic 20% Injection that is prepared and sold by the Baxter international Inc. can be used as a most preferred composition of the present invention.

The degenerative brain disease can be at least one disease selected from a group consisting of dementia, Alzheimer's disease, Huntington's chorea, Parkinson's disease, Pick's disease and Creutzfeld-Jacob disease. However, the degenerative brain diseases are not limited to the said group and can include all diseases that can be benefited by the composition of the present invention.

The present invention provides a health functional food for preventing or ameliorating stroke or degenerative brain disease including at least two substances selected from the group consisting of egg yolk lecithin, glycerol, sodium oleate, medium chain triglyceride and refined fish oil; olive oil; and soybean oil.

As a preferred embodiment of the present invention, the health functional food includes 0.1-20 wt % of olive oil, 0.1-20 wt % of soybean oil, 0.1-20 wt % of medium chain triglyceride and 0.1-10 wt % of refined fish oil. More preferably, the health functional food includes 6 wt % of olive oil, 6 wt % of soybean oil, 6 wt % of medium chain triglyceride and 3 wt % of refined fish oil. The composition ratio was a result of the inventors' research on a composition which would exhibit low toxicity and side effect while having superior neuroprotective effect. SMOFlipid 20% Injection that is manufactured and sold by the Fresenius-Kabi Korea© can be used as a most preferred health functional food of the present invention.

As a preferred embodiment of the present invention, the health functional food includes 1-50 wt % of olive oil, 0.1-20 wt % of soybean oil, 0.01-5 wt % of egg yolk lecithin, 2.25 wt % of glycerol and 0.01-1 wt % of sodium oleate. More preferably, the health functional food includes 16 wt % of olive oil, 4 wt % of soybean oil, 1.2 wt % of egg yolk lecithin, 2.25 wt % of glycerol and 0.03 wt % of sodium oleate. The composition ratio was a result of the inventors' research on a composition which would exhibit low toxicity and side effect while having superior neuroprotective effect. Clinoleic 20% Injection that is manufactured and sold by the Baxter International Inc. can be used as a most preferred health functional food of the present invention.

The present invention also provides a method of preventing, ameliorating or treating stroke or degenerative brain disease by administering a composition including at least two substances selected from a group consisting of therapeutically effective amount of egg yolk lecithin, glycerol, sodium oleate, medium chain triglyceride and refined fish oil; olive oil; and soybean oil to a subject in need of treatment.

As a preferred embodiment of the present invention, the composition includes 0.1-20 wt % of olive oil, 0.1-20 wt % of soybean oil, 0.1-20 wt % of medium chain triglyceride, and 0.1-10 wt % of refined fish oil. More preferably, the composition includes 6 wt % of olive oil, 6 wt % of soybean oil, 6 wt % of medium chain triglyceride, and 3 wt % of refined fish oil. SMOFlipid 20% Injection that is manufactured and sold by the Fresenius-Kabi Korea© can be used as a most preferred composition of the present invention.

As a preferred embodiment of the present invention, the composition includes 1-50 wt % of olive oil, 0.1-20 wt % of soybean oil, 0.01-5 wt % of egg yolk lecithin, 2.25 wt % of the glycerol and 0.01-1 wt % of the sodium oleate. More preferably, the composition includes 1.6 wt % of olive oil, 4 wt % of soybean oil, 1.2 wt % of egg yolk lecithin, 2.25 wt % of glycerol and 0.03 wt % of sodium oleate. Clinoleic 20% Injection that is manufactured and sold by the Baxter International Inc. can be used as a most preferred composition of the present invention.

The wording "therapeutically effective amount" is directed to an amount of active ingredients or pharmaceutical compositions which induce biological or medical reaction from animals or human beings that is considered by researchers, veterinarians, doctors or other therapists. It includes an amount inducing alleviation of symptoms of diseases or disorders to be treated. It is obvious to those skilled in the art that therapeutically effective dose and frequency of the active ingredients of the present invention would vary depending on desired effects.

Advantageous Effect

The composition of the present invention has no toxicity and side effects while having superior neuroprotective effect, thus it can be effectively and safely used for preventing, treating or ameliorating stroke or degenerative brain disease.

BRIEF DESCRIPTION OF THE DRAWINGS

FIG. 1 is an image showing a result of an observation via TTC staining on brain slices of a control group wherein a saline solution is administered to middle cerebral artery occlusion model rats, and experimental groups wherein oleic acid, a sodium oleate solution, the Clinoleic20% or the SMOFlipid20% is administered to middle cerebral artery occlusion model rats.

FIG. 2 is a graph illustrating comparison in damage rates of brain tissue (infarction area) in the control group, and the experimental groups of the middle cerebral artery occlusion model animals wherein the oleic acid, the sodium oleate solution, the Clinoleic20% or the SMOFlipid20% is administered.

DESCRIPTION OF THE PREFERRED EMBODIMENTS

The inventors confirmed that the pharmaceutical composition for preventing or treating stroke or degenerative brain disease comprising at least two substances selected from the group consisting of egg yolk lecithin, glycerol, sodium oleate, medium chain triglyceride and refined fish oil; olive oil; and soybean oil has superior neuroprotective effect for neuronal cell damages caused by cerebral ischemia, and that the pharmaceutical composition has less toxicity and side effects upon result of low death rate after administration in the middle cerebral artery occlusion model (MCAo), and succeedingly completed the present invention.

The present invention will be described more in detail hereinafter.

Pharmaceutical Composition

The pharmaceutical composition of the present invention includes at least two substances selected from the group consisting of egg yolk lecithin, glycerol, sodium oleate, medium chain triglyceride and refined fish oil; olive oil; and soybean oil.

The composition of the present invention can be administered orally or parenterally, more preferably be administered parenterally, and most preferably be administered intravenously. In case of formulation, it can be prepared by using conventional diluents or excipients such as a filler, an extender, a binder, a humectants, a disintegrant and a surfactant.

Formulation for parenteral administration includes a sterile aqueous solution, a nonaqueous solution, a suspension, an emulsifiable concentrate, a lyophilized formulation and a suppository. Propylene glycol, polyethylene glycol, vegetable oil and an injectable ester such as ethyl oleate, etc. can be used as a nonaqueous solvent and a solvent for suspension. Witepsol, macrogol, tween61, cacao butter, laurinum, glycerol, gelatin, etc. can be used as a base of the suppository. The pharmaceutical composition of the present invention can be administered hypodermically, intravenously and intramuscularly when administering parenterally.

Dosage of the pharmaceutical composition of the present invention can vary depending on the patient's condition, weight, degree of disease, drug form, administration passage and period, and it can be selected properly by those skilled in the art. However, it is preferred to administer 0.1-1000 mg/kg of the composition of the present invention per a day to achieve desirable effect. Administration frequency can be once or several times per a day. However, the said dosage does not limit the scope of the present invention.

The composition of the present invention can be used for preventing or treating stroke or degenerative brain disease solely or jointly with an operation, hormone therapy, chemotherapy and methods using biological response regulators.

Health Functional Food

The present invention provides the health functional food for preventing or ameliorating stroke or degenerative brain disease comprising at least two substances selected from the group consisting of egg yolk lecithin, glycerol, sodium oleate, medium chain triglyceride and refined fish oil; olive oil; and soybean oil.

The health functional food of the present invention can be used by adding at least two substances selected from the group consisting of egg yolk lecithin, glycerol, sodium oleate, medium chain triglyceride and refined fish oil, olive oil, and soybean oil intactly, or with other food or food ingredients, and can be used according to conventional methods. Content of the active ingredients can be adequately adjusted according to a purpose of use (e.g. for prevention, health or therapeutic purpose). In general, components of the present invention can be added in an amount of 0.01-50 wt % of total food weight when preparing food or beverage.

Additionally, types of the food are not specifically limited. Examples of foods that the pharmaceutical composition of the present invention can be added thereto could be beverages, gums, vitamin complexes, drink preparations among others and furthermore, the food includes all conventional health functional foods.

Like other common beverages, beverage composition of the present invention can include various flavoring agents or natural carbohydrates, etc. as additional ingredients. The natural carbohydrates can be general sugars such as monosaccharides (e.g. glucose and fructose among others); disaccharides (e.g. maltose and sucrose among others); and polysaccharides (e.g. dextrin and cyclodextrin among others); and sugar alcohols such as xylitol, sorbitol and erythritol among others. Furthermore, other flavoring agents which are not mentioned before can also be used (e.g. saccharin and aspartame among others).

The health functional food of the present invention can include various nutritional supplements, vitamin, minerals (e.g. electrolyte), synthetic flavoring agents, coloring agents and enhancers (e.g. cheese and chocolate among others), pectic acid and salt thereof, alginic acid and salt thereof, organic acid, protective colloid thickener, pH modifier, stabilizing agent, preservative, glycerin, alcohol and carbonator which is used for carbonated drinks among others.

Preparation Method

The pharmaceutical composition and the health functional food of the present invention can be prepared by conventional methods. The pharmaceutical composition and the health functional food can be prepared by mixing at least two substances selected from the group consisting of egg yolk lecithin, glycerol, sodium oleate, medium chain triglyceride and refined fish oil; olive oil; and soybean oil, and by selectively mixing pharmaceutically or nutritionally acceptable excipients, diluents or other additives.

For an example, the composition was prepared by mixing olive oil, soybean oil, medium chain triglyceride, refined fish oil and distilled water. The ingredients were mixed by using a homogenizer, and were mixed several more times by using a high pressure homogenizer, resulting in the composition of the present invention.

As an another example, the composition was prepared by mixing olive oil, soybean oil, egg yolk lecithin, glycerol, sodium oleate and distilled water. The ingredients were mixed by using a homogenizer, and were mixed, several more times by using a high pressure homogenizer, resulting in the composition of the present invention.

Practical and presently preferred embodiments of the present invention are illustrative as shown in following Example, Experimental Examples and Comparative Example. However, it will be appreciated that those skilled in the art, on consideration of this invention, may make modifications and improvements within the spirit and scope of the present invention.

EXAMPLE

The SMOFlipid 20% Injection that is manufactured and sold by the Fresenius-Kabi Korea©, and the Clinoleic 20% Injection that is manufactured and sold by the Baxter International Inc. were used as the compositions of the present invention comprising at least two substances selected from the group consisting of the egg yolk lecithin, the glycerol, the sodium oleate, the medium chain triglyceride and the refined fish oil; the olive oil; and the soybean oil. 100 ml of the SMOFlipid20% Injection comprises 6 g of the purified soybean oil, 6 g of the purified olive oil, 6 g of the medium chain triglyceride and 3 g of the refined fish oil. 100 ml of the Clinoleic20% Injection includes 16 g of the purified olive oil, 4 g of the purified soybean oil, 1.2 g of the egg yolk lecithin, 2.25 g of the glycerol and 0.03 g of the sodium oleate.

Comparative Example

The oleic acid and the sodium oleate solution were used as compositions for comparison with the effects of the Clinoleic20% Injection and the SMOFlipid20% Injection of the present invention.

The oleic acid was purchased from Sigma Aldrich Korea (Catalog No. 01008). The sodium oleate is the sodium salt of the oleic acid and is more soluble to water because it is in form of powder unlike the oleic acid. The sodium oleate was purchased from Sigma Aldrich Korea (Catalog No. 07501). The sodium oleate solution was prepared by adding 0.25 ml of the glycerol into the 10 mg of the sodium oleate and vortexing; mixed with triple distilled water (Millipore DQ-3) to have total 10 ml of volume; and comminuted for three hours by using a sonicator.

Experimental Example 1: Neuroprotective Effect of the Composition of the Present Invention—Middle Cerebral Artery Occlusion Model (MCAo)

1.1. Preparation of Laboratory Animals 8 week-old adult male Sprague-Dawley (SD) rats, obtained from Samtako (Korea), weighing 300 g were kept in an environment to adapt to the experimental environment while providing enough feed and water. After one week of adaptation period, the animals were used for the following experiments.

1.2. Preparation of Middle Cerebral Artery Occlusion Model

Intraluminal suture method was used to measure neuroprotective effect of the oleic acid, the sodium oleate solution, the SMOFlipid20% and the Clinoleic20% on neuronal cell damage caused by local cerebral ischemia (Zea Longa, et al., Stroke, 20:84-91, 1989).

In detail, a nylon suture (4-0, 22 mm) was prepared by silicone coating about 5-8 mm of the end of the suture to have 0.36 mm of diameter, and was used for experiment. The rats prepared in Experimental Example 1.1 were anesthetized with 5% of isoflurane in a mixture of gas (i.e. 70% $N_2O$ and 30% $O_2$). A syringe was inserted in one side for blood collection and a probe was inserted in the other side to measure blood pressure. Then the blood glucose level and the blood gas level in the collected blood were measured.

Through midline neck incision, right carotid artery and external carotid artery (ECA), which are branches of external carotid artery, were separated. Superior thyroid artery and laryngeal artery were cauterized by using an electrocauter and a probe was introduced from external carotid artery to internal carotid artery by inserting it about 18-19 mm from the common carotid artery branch and fixing it with a suture. After suturing the skin incision and the rats were allowed to recover from anesthesia. Same number of animals were induced in all experimental groups in the very day and observed the operation while maintaining 37 g 0.5° C. of body temperature. The rats were anesthetized again in the same way as the above after 90 minutes of the operation and the probe was withdrawn to allow reperfusion.

24 hours after the reperfusion, the animals were sacrificed by cervical spine dislocation. The brains were removed within two minutes and six 2 mm thick slices were obtained. Then the tissue slices were immersed in a 12-well plate containing 2% TTC (triphenyltertrazolium chloride) solution for 30 minutes at 37° C., and the tissue slices were fixed with 4% paraformaldehyde for observation. All operation procedures were conducted beneath an operating microscope. The body temperature was controlled not to drop below 37° C. by using a heat lamp and isofluran was maintained at 2% in the course of anesthesia. Each stained brain tissue slice was photographed one by one by using a digital camera. The files were stored in a computer, and the infarct area (%) in each tissue slice was calculated according to the following equation 1 by using an analysis program (i.e. Optimas 6.5, Bioscan). The adjusted volume of the infarct area was calculated through following Equation 2.

Infarct area(%)=(A−B/A)s 100     [Equation 1]

A: volume of normal left hemisphere
B: adjusted infarct volume ($mm^3$)

Adjusted infarct volume ($mm^3$)=(volume of normal left hemisphere)−(normal area in damaged hemisphere)     [Equation 2]

1.3. Administration of Clinoleic 20%, SMOFlipid20%, Oleic Acid and Sodium Oleate Solution Right after ischemia induction, to Example groups, 200 mg/kg of the Clinoleic20% (based on fatty acid) or 500 mg/kg of the SMOFlipid20% (based on fatty acid) was administered intravenously in a volume of 0.3 ml per 100 g of rat weight; to Comparative Example groups, 100 mg/kg of the oleic acid or 3 mg/kg of the sodium oleate solution was administered intravenously in a volume of 0.3 ml per 100 g of rat weight; and to control group, same volume of saline solution was administered.

1.4. Neuroprotective Effect

Upon measurement of brain tissue and neuroprotective effect of each Clinoleic20%, SMOFlipid20%, oleic acid and sodium oleate solution, groups in which Clinoleic20%, SMOFlipid20%, oleic acid or sodium oleate solution was administered respectively had less TTC-unstained area due to neuronal cell death, and TTC-stained dark-red colored area was found to be large because neuronal cells were not damaged compared to the control group. For reference, when brain tissue is stained with TTC, area where neuronal cell death incurred due to damage would not be stained and be shown as white color, and normal area would be stained and be shown as dark-red color (see FIG. 1).

Upon evaluation of protective effect on neuronal cell death induced by middle cerebral artery occlusion, significant efficacy was shown in every group, especially 47% of high neuroprotective effect was shown in Clinoleic20% group ($p<0001$) (see FIG. 2).

Experimental Example 2: Safety Evaluation—the Death Rate of Experimental Animals Right after degenerative brain disease induction, death rate was calculated by counting number of dead animals in every group from the time of administration until they were sacrificed.

Following Table 1 shows death rate of the animals of the control group and the experimental groups in the middle cerebral artery occlusion model.

TABLE 1

| Group | Number of Administered Animals | Number of Dead Animals | Death Rate (%) |
|---|---|---|---|
| Oleic Acid | 116 | 21 | 18.1 |
| Sodium Oleate | 37 | 8 | 21.6 |
| Clinoleic20% | 114 | 5 | 4.3 |
| SMOFlipid20% | 21 | 0 | 0 |

As shown in Table 1, in case of the experimental group in which oleic acid was administered to brain infarction induced rats, 21 rats died out of 116 rats and death rate was 181%, and the death rate was highest as 21.6% in sodium oleate solution administered group where 8 rats died out of 37 rats. On the other hand, death rate of Clinoleic20% administered, group was 4.3% with 2 deaths out of 88 rats, and no rats died in the SMOFlipid20% administered group.

What is claimed is:

1. A method for ameliorating or treating stroke or neuronal cell damage caused by cerebral ischemia in a subject in need thereof, comprising administering to the subject a therapeutically effective amount of a composition consisting essentially of olive oil, soybean oil, and: (a) egg yolk lecithin, glycerol, and sodium oleate or (b) medium chain triglyceride and refined fish oil.

2. The method of claim 1, wherein the composition consists essentially of 0.1-20 wt % of the olive oil, 0.1-20 wt % of the soybean oil, 0.1-20 wt % of the medium chain triglyceride, and 0.1-10 wt % of the refined fish oil.

3. The method of claim 1, wherein the composition consists essentially of 1.0-50 wt % of the olive oil, 0.1-20 wt % of the soybean oil, 0.01-5 wt % of the egg yolk lecithin, 2.25 wt % of the glycerol and 0.01-1 wt % of the sodium oleate.

* * * * *